United States Patent
Kovi et al.

(10) Patent No.: US 9,822,145 B2
(45) Date of Patent: Nov. 21, 2017

(54) METHODS OF MAKING CARFILZOMIB AND INTERMEDIATES THEREOF

(71) Applicant: Apicore US LLC, Somerset, NJ (US)

(72) Inventors: Ravishanker Kovi, Monroe, NJ (US); Jayaraman Kannapan, Gujarat (IN); Vasanthakumar G Ramu, Karnataka (IN); Alaparthi Lakshmi Prasad, Vadodara (IN); Talluri Bhushaiah Chowdary, Tenali (IN); Gaurav Kulkarni, Gujarat (IN); Saiyed Akeel Ahmed Shakeel Ahmed, Vadodara (IN); Veerabhadra Rao Bobbili, Andhra Pradesh (IN); N V Raghavalu Dusanapudi, Andhra Pradesh (IN); Anand V. Mantri, Vadodara (IN)

(73) Assignee: Apicore US LLC, Somerset, NJ (US)

( * ) Notice: Subject to any disclaimer, the term of this patent is extended or adjusted under 35 U.S.C. 154(b) by 0 days.

(21) Appl. No.: 15/228,689

(22) Filed: Aug. 4, 2016

(65) Prior Publication Data

US 2016/0340388 A1   Nov. 24, 2016

Related U.S. Application Data

(62) Division of application No. 14/923,068, filed on Oct. 26, 2015.

(60) Provisional application No. 62/068,928, filed on Oct. 27, 2014.

(51) Int. Cl.
*A61K 38/00* (2006.01)
*C07K 5/00* (2006.01)
*C07K 7/00* (2006.01)
*C07K 16/00* (2006.01)
*C07K 17/00* (2006.01)
*C07K 5/107* (2006.01)
*C07K 5/065* (2006.01)

(52) U.S. Cl.
CPC ........ *C07K 5/1016* (2013.01); *C07K 5/06078* (2013.01)

(58) Field of Classification Search
CPC .................. C07K 5/06078; C07K 5/1016
See application file for complete search history.

(56) References Cited

U.S. PATENT DOCUMENTS

| 4,242,507 | A | 12/1980 | Itoh et al. |
| 5,331,006 | A * | 7/1994 | Horwell ............ C07D 207/327 514/481 |
| 7,232,818 | B2 | 6/2007 | Smyth |
| 7,417,042 | B2 | 8/2008 | Smyth |
| 8,198,270 | B2 | 6/2012 | Smyth |
| 8,207,124 | B2 | 6/2012 | Smyth |
| 8,207,125 | B2 | 6/2012 | Smyth |
| 8,207,297 | B2 | 6/2012 | Smyth |
| 2005/0245435 | A1 | 11/2005 | Smyth |
| 2007/0105786 | A1 | 5/2007 | Zhou |
| 2008/0090785 | A1 | 4/2008 | Smyth et al. |
| 2008/0200398 | A1 | 8/2008 | Smyth |
| 2009/0105156 | A1 | 4/2009 | Phiasivongsa |
| 2010/0240903 | A1 | 9/2010 | Phiasivongsa |
| 2013/0150290 | A1 | 6/2013 | Phiasivongsa |

FOREIGN PATENT DOCUMENTS

| CN | 103360348 A | 10/2013 | |
| CN | 103641890 A | 3/2014 | |
| WO | WO2009045497 | * 4/2009 | ............... C07K 5/10 |
| WO | WO2015010436 | * 1/2015 | ............. C07K 5/117 |

OTHER PUBLICATIONS

Nyfeler. Peptide Synthesis via Fragment Condensation. vol. 35 Methods in Molecular Biology, 1994, pp. 303-316.*
CN103641890. Yao et al. Machine translation from Chinese to English. Mar. 2014. 53 pages.*
Morrison and Boyd. Alkaline Hydrolysis of Esters. Organic Chemistry, 6ht Ed., 1992, p. 773.*
Kyung Bo Kim, et al., "Development and Characterization of Proteasome Inhibitors" Methods Enzymol. 399, 585-609 (2005).
Han-Jie Zhou, etal., Design and Synthesis of an Orally Bioavailable and Selective Peptide Epoxyketone Proteasome Inhibitor (PR-047) Journal of Medicinal Chemistry, vol. 52, pp. 3028-3038 (2009).
International Search Report and Written Opinion for corresponding PCT Application No. PCT/US15/57381, 10 pages dated Feb. 16, 2016.
Office Action for corresponding U.S. Appl. No. 14/923,068, 15 pages, dated May 3, 2017.
Brian L. Bray "Large Scale Manufacture of Peptide Therapeutics by Chemical Synthesis" Nature REviews—Drug Sicovery vol. 2, pp. 587-593 (Jul. 2003).
Albericio et al., "Chemical Approaches to the Synthesis of Peptides and Proteins" CRC Press (1997).

* cited by examiner

*Primary Examiner* — Marcela M Cordero Garcia
(74) *Attorney, Agent, or Firm* — Timothy X. Gibson, Esq.; Gibson & Dernier LLP

(57) ABSTRACT

Racemization-free methods are disclosed for the synthesis of carfilzomib. Novel intermediates and methods of making carfilzomib employing fragment condensation using the novel intermediates are disclosed. Amorphous carfilzomib and methods of making same are disclosed.

15 Claims, 1 Drawing Sheet

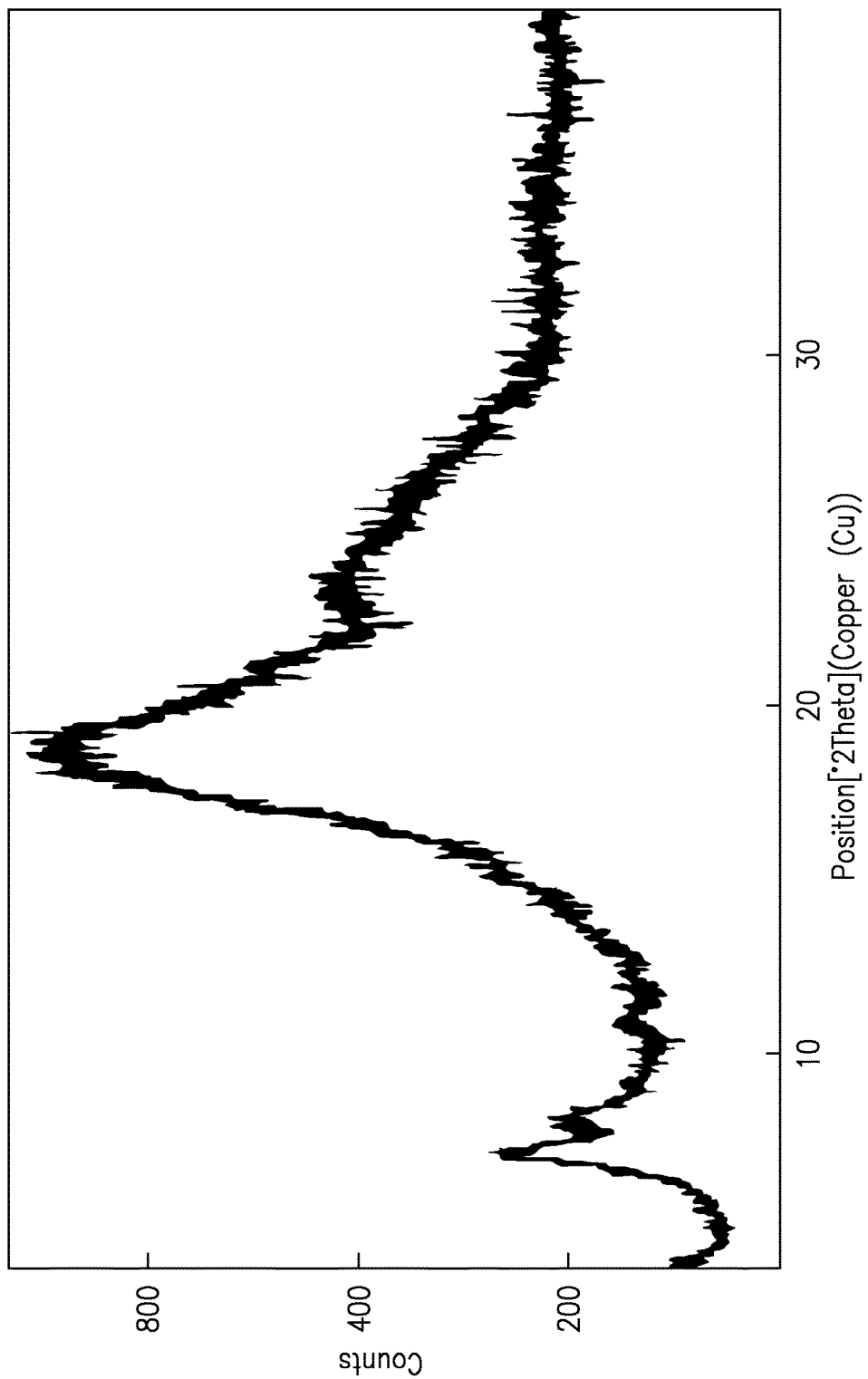

METHODS OF MAKING CARFILZOMIB AND INTERMEDIATES THEREOF

CROSS-REFERENCE TO RELATED APPLICATIONS

This application is a divisional of U.S. patent application Ser. No. 14/923,068 filed Oct. 26, 2015 and claims the benefit of U.S. Provisional Application No. 62/068,928 filed Oct. 27, 2014, the entireties of which are incorporated herein by reference.

FIELD OF THE INVENTION

The presently disclosed subject matter relates to the synthesis of carfilzomib.

BACKGROUND

Carfilzomib, an epoxomicin derivative, is a selective proteasome inhibitor. Carfilzomib is used to treat patients with multiple myeloma who have already been treated with at least two other medications.

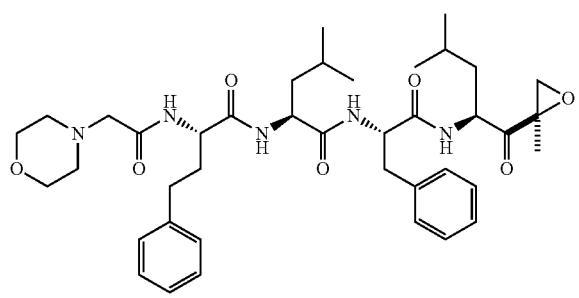

Carfilzomib

SUMMARY OF THE INVENTION

Novel methods and intermediates are disclosed for the production of carfilzomib. Processes disclosed herein may be employed to produce amorphous form carfilzomib.

In one or more embodiments methods employ a fragment-based approach involving active esters. For example, active esters obtained from hydroxyl-benzotriazoles, hydroxy-azabenzotriazoles, succinimide esters, substituted phenols, etc. may be employed. The methods are efficient and highly reproducible in large scale industrial processes. The methods employ fragment condensation using novel synthetic intermediates and provide racemization-free approaches. The disclosed methods produce carfilzomib in a reduced number of steps compared to existing methods in the literature. In accordance with an embodiment powder x-ray diffraction reveals the resulting carfilzomib active pharmaceutical ingredient (API) made according to a method disclosed herein is in amorphous form.

In one embodiment compounds having the formula I and pharmaceutically active esters and salts thereof are disclosed wherein Y is 1-hydroxybenzotriazole, azabenzotriazole-succinimidyl, pentafluorophenyl, trichlorophenyl, nitrophenyl, pentachlorophenyl, 3,4-dehydro-4-oxo-1,2,3-benzotriazinyl (Dhbt), or fluorenylmethyl.

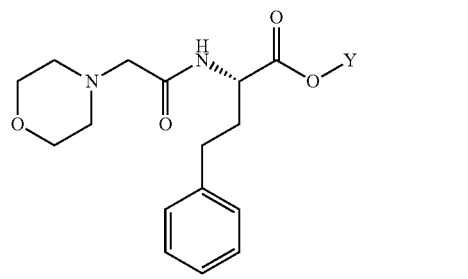

I

Compounds of formula I may include active esters obtained from corresponding hydroxy compounds and substituted phenols. Compounds of formula I may be employed as intermediates in methods disclosed herein for making carfilzomib.

In further embodiments, methods of making compounds of formula I and derivatives thereof are disclosed.

In some embodiments active esters of formula I may be synthesized using reagents such as carbonyldiimidazole (CDI), 1-ethyl-3-(3-dimethylaminopropyl)carbodiimide (EDC), N,N'-dicyclohexylcarbodiimide (DCC), and N,N'-diisopropylcarbodiimide (DIPC).

In some embodiments, methods involve obtaining a free acid of a compound of formula I by various chemical methods and activating a resulting intermediate using a hydroxy and/or phenolic compound. Examples of such chemical methods include but are not limited to bis-silylation, using silylating agents, an organic base, and/or hydrolysis of esters by using alkali metal hydroxides including NaOH, KOH, LiOH and their corresponding carbonates, etc.

Compounds of formula I may be isolated using various organic solvents including but not limited to methanol, ethanol, acetonitrile, MDC, chloroform, ethylacetate, etc.

In other embodiments, compounds having the general structure IA, are disclosed

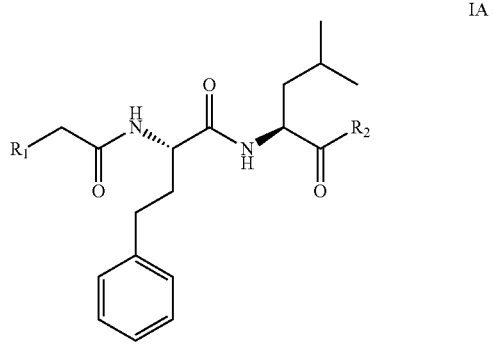

IA wherein Y, $R_1$ and $R_2$ are as defined in Table I for compounds having the formulas II, III, and IV.

TABLE 1

| Compound | $R_1$ | $R_2$ |
|---|---|---|
| 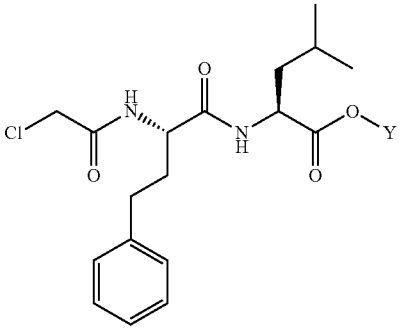<br>II | Chloro | O—Y |
| 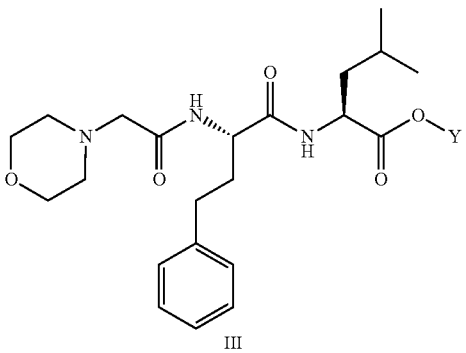<br>III | Morpholino | O—Y |
| 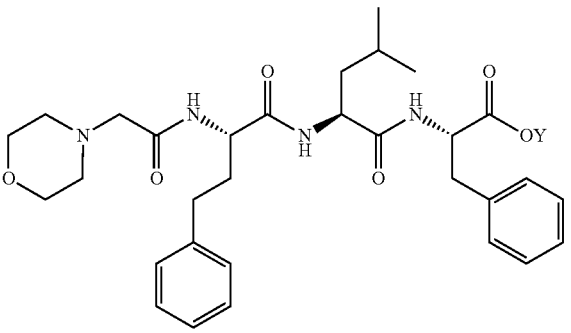 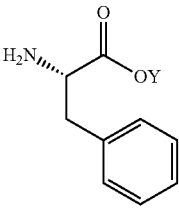<br>IV | Morpholino | |

Y = 1-hydroxybenzotriazole, azabenzotriazole, succinimidyl, pentafluorophenyl, trichlorophenyl, nitrophenyl, pentachlorophenyl, 3,4-dehydro-4-oxo-1,2,3-benzotriazinyl (Dhbt), or fluoroenylmethyl.

The compounds of formula II, III, and IV and derivatives thereof, including stable active esters, are useful as intermediates in the synthesis of carfilzomib.

Formula II, III and IV active esters may be obtained from corresponding hydroxy compounds and phenols.

In further embodiments, methods of making compounds of formula II, III, and IV and derivatives thereof are disclosed.

In some embodiments active esters of formulas II, III, and IV may be synthesized using reagents such as CDI, EDC, DCC, and DIPC.

In some embodiments, methods involve obtaining a free acid of a compound of formula II, III, and IV by various chemical methods and activating a resulting intermediate using a hydroxy and/or phenolic compound. Examples of such chemical methods include but are not limited to bis-silylation, using silylating agents, an organic base, and/or hydrolysis of esters by using alkali metal hydroxides including NaOH, KOH, LiOH and their corresponding carbonates, etc.

Compounds of formula II, III, and IV may be isolated using various organic solvents including but not limited to methanol, ethanol, acetonitrile, MDC, chloroform, ethylacetate, etc.

Purification of compounds I, II, III and IV may be effected using any suitable technique including but not limited to preparative RP-HPLC.

In other embodiments methods are disclosed for making carfilzomib by employing a compound of the formula I or derivatives thereof using a 2+2+1 fragment condensation.

In other embodiments methods are disclosed for making carfilzomib by employing a compound of the formula I (A) or derivatives thereof using a 3+2 fragment condensation.

In other embodiments methods are disclosed for making carfilzomib by employing a compound of the formula II or derivatives thereof using a 3+2 fragment condensation.

In other embodiments methods are disclosed for making carfilzomib by employing a compound of the formula III or derivatives thereof using a 3+2 fragment condensation.

In accordance with another embodiment, a method of making amorphous form carfilzomib is disclosed which employs the synthetic route:

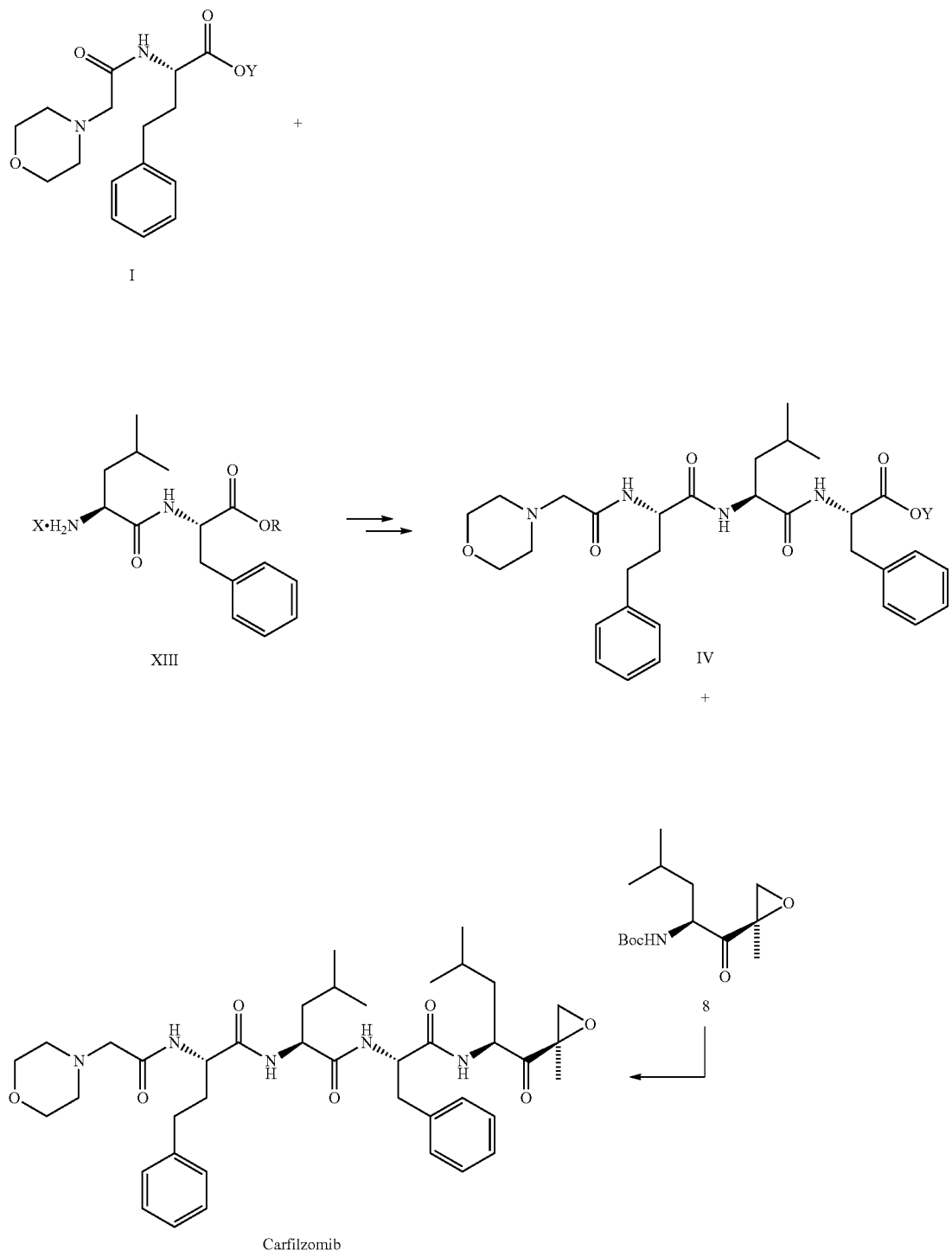

wherein Y is 1-hydroxybenzotriazo, azabenzotriazolc, succinimidyl, pentafluorophenyl, trichlorophenyl, nitrophenyl, pentachlorophenyl 3,4-dehydro-4-oxo-1,2,3-benzotriazinyl (Dhbt), or fluorenylmethyl; X is HCl, trifluoroacetic acid (TFA), HCOOH, p-toluenesulfonic acid (TsOH), or methanesulfonic acid (MsOH); and R is H, methyl (Me), ethyl (Et), benzyl (Bzl), or isopropyl (iPr).

In accordance with another embodiment, a method of making amorphous form carfilzomib is disclosed which employs the synthetic route:

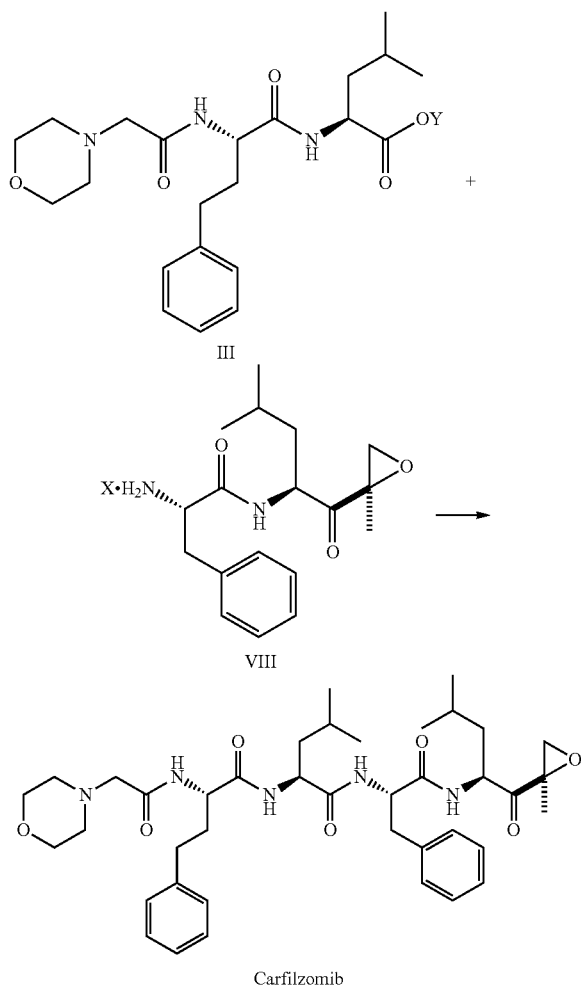

wherein Y is 1-hydroxybenzotriazole, azabenzotriazole, succinimidyl, pentafluorophenyl, trichlorophenyl, nitrophenyl, pentachlorophenyl, 3,4-dehydro-4-oxo-1,2,3-benzotriazinyl (Dhbt), or fluorenylmethyl and X is HCl, TFA, HCOOH, TsOH, MsOH or isopropyl (IPr).

Amorphous carfilzomib may be isolated using organic solvent extraction wherein the solvent may be MDC, chloroform, ethylacetate, diethylether, methyl-tert-butyl ether, diisopropyl ether, etc.

In another embodiment, amorphous form of carfilzomib is disclosed. X-ray powder diffraction data of amorphous carfilzomib made in accordance with a method disclosed herein is shown in FIG. 1.

BRIEF DESCRIPTION OF THE DRAWINGS

For the purposes of illustration, there are forms shown in the drawings that are presently preferred, it being understood, however, that the invention is not limited to the precise arrangements and instrumentalities shown.

FIG. 1 is a graphical depiction of powder XRD data of a batch of carfilzomib made in accordance with at least one embodiment of the present disclosure.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Methods

The present invention describes in one aspect the synthesis of amorphous carfilzomib by employing active esters as novel intermediates.

Scheme I

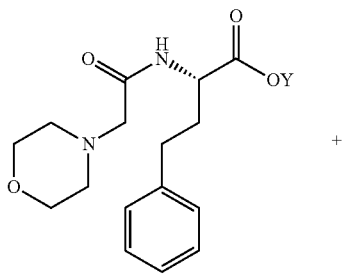

I

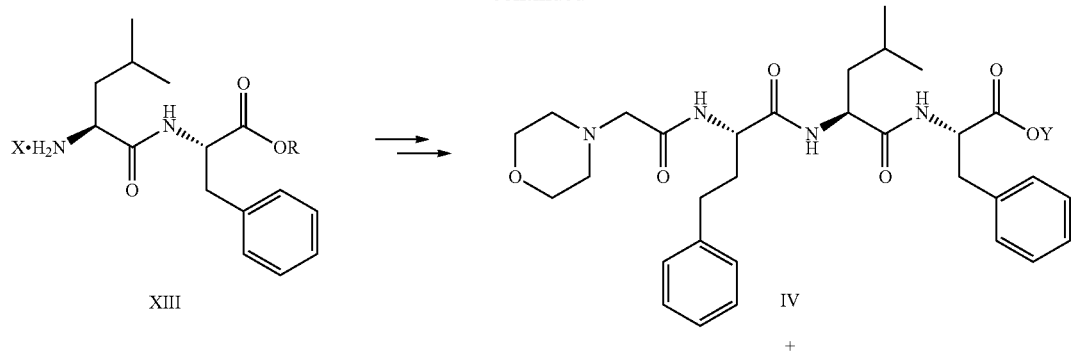
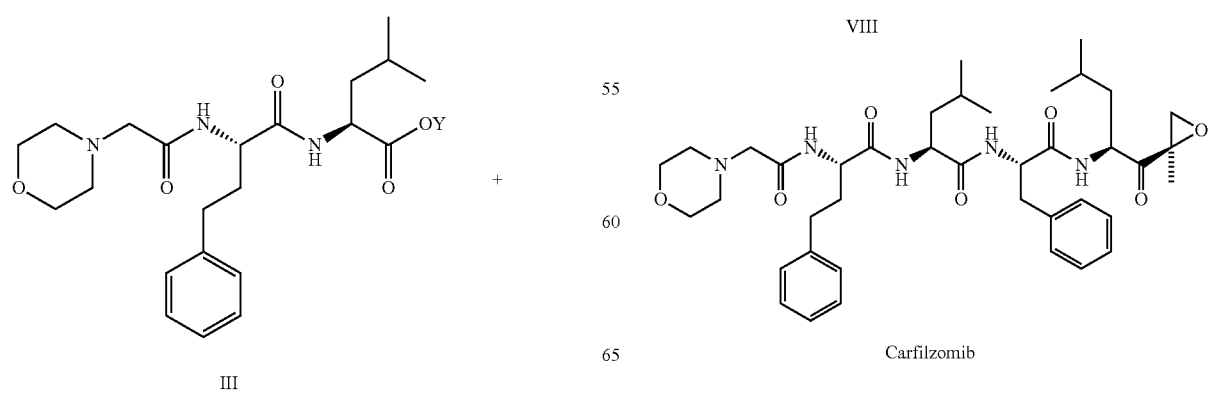
wherein Y is 1-hydroxybenzotriazole, azabenzotriazole, succinimidyl, pentafluorophenyl, trichlorophenyl, nitrophenyl, pentachlorophenyl, 3,4-dehydro-4-oxo-1,2,3-benzotriazinyl (Dhbt), or fluorenylmethyl,
X is HCl, TFA, HCOOH, TsOH, or MsOH, and
R is H, methyl (Me), ethyl (Et), benzyl (Bzl), or isopropyl (IPr).
Scheme II wherein Y is 1-hydroxybenzotriazolelt, azabenzotriazole, succinimidyl, pentafluorophenyl, trichlorophenyl, nitrophenyl, pentachlorophenyl, 3,4-dehydro-4-oxo-1,2,3-benzotriazinyl (Dhbt), or fluorenylmethyl; and X is HCl, trifluoroacetic acid (TFA), HCOOH, p-toluenesulfonic acid (TsOH), or methanesulfonic acid (MsOH) or isopropyl (iPr).

EXPERIMENTS AND EXAMPLES

Example 1(a)

Morpholine Derivative-Dipeptide Acid (One Pot)

To a solution of morpholin-4-yl-acetic acid (100.0 mmol) in 250 ml dry tetrahydrofuran (THF), isobutyl chloroformate (100.0 mmol) and N-methylmorpholine (NMM) (110.0 mmol) were added and the mixture was stirred at 0° C. for 30 min. In another flask, homo-phenylalanine (100.0 mmol), trimethylsilyl chloride (TMS-Cl) (200 mmol) and diisopropylethylamine (DIPEA) (200 mmol) were refluxed in 300 mL of dry dichloromethane for 1 h. The mixture was cooled to 0° C. and added in one portion to a preformed mixed anhydride of formula 1a and the combined reaction mixture was stirred for 30-45 min. The reaction was concentrated under reduced pressure and the residue was dissolved in 10% $Na_2CO_3$ and washed with ether. The aqueous phase was acidified with 1N HCl and extracted with 500 mL EtOAc/ dichloromethane (MDC). The organic layer was washed with water (2×200 mL) and brine (1×200 mL) and dried over anhydrous $Na_2SO_4$. The $Na_2SO_4$ was removed by filtration and the solvent evaporated under reduced pressure to give a dipeptide acid of the formula Ib.

Example 1(b)

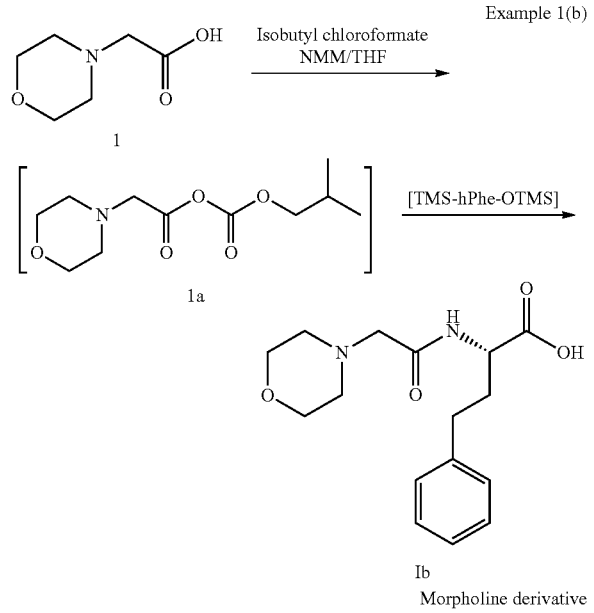

Ib
Morpholine derivative

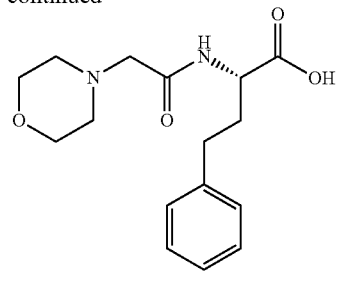

Ib

To a 500 mL three-neck round bottom flask equipped with a magnetic stirrer and thermometer pocket arranged in a tub was charged a chloroacetamido derivative of H-hPhe-OH (10.0 g) of formula 3, THF (100 mL) and the reaction mixture was stirred at 20-30° C. KI (0.25 equiv.) and morpholine (1.2 equiv.) were added dropwise into the reaction mass at 5-15° C. After 15 minutes the temperature was increased to 20-30° C. The reaction was maintained for 12 to 16 h and upon confirmation of completion of the reaction, the solvent was distilled completely under vacuum at below 40° C. The residue was dissolved in MDC (300 mL) and washed with process water and brine solution. The organic layer was dried over anhydrous sodium sulphate (5 g) and distilled under vacuum at below 40° C. The compound Ib was precipitated with diethyl ether (150 mL) and filtered.

Example 2

Preparation of Chlroacetamido Derivative of Homophenylalanine Methyl Ester

A 500 mL three-neck round bottom flask equipped with a mechanical stirrer and thermometer pocket was arranged in a tub. A hydrochloride salt of H-hPhe-OMe (30 g) and MDC (200 mL) were charged into the flask and stirred under nitrogen atmosphere. Triethylamine (2 equiv.) was slowly added into the reaction mass at 0° C. to 10° C. and stirred for 10 min., followed by chloroacetyl chloride (1.1 equiv.) added drop wise at 0° C. to 10° C. with vigorous stirring. After 15 min. the temperature of the reaction mixture was raised to 30° C. and maintained 3 h. Upon completion of the reaction (confirmed by TLC), the reaction mass was diluted with MDC (200 mL), quenched with process water and washed with process water (2×200 mL) and brine (200 mL). The organic layer was dried over anhydrous sodium sulfate (10 g) and concentrated under vacuum at below 40° C. and precipitated by adding diethyl ether.

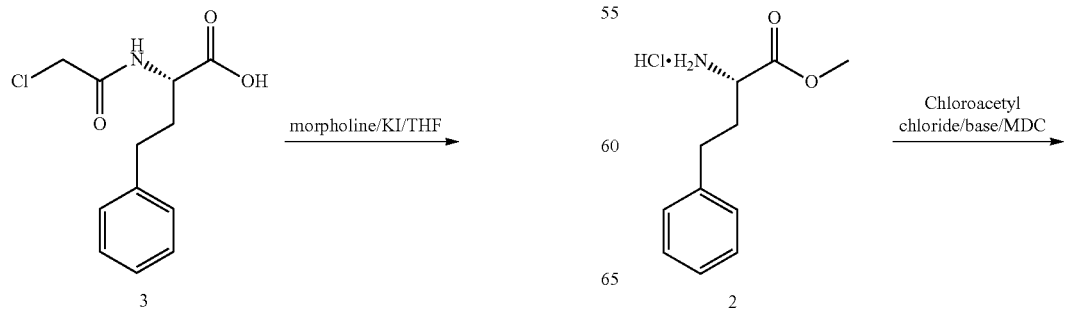

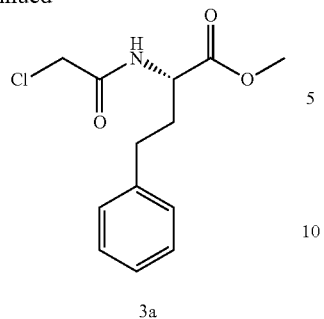

3a

Example 3(a)

Morpholine Derivative-Dipeptide Ester

A 500 mL single neck flask equipped with a magnetic stirrer was arranged in a tub. Morpholine-4-yl-acetic acid (100 mmol) and DMF (200 mL) were charged into the flask and stirred at 20-30° C. DIPEA (100 mmol) was added slowly into the reaction mixture at 20-30° C., followed by addition of 2-(1H-benzotriazole-1-yl)-1,1,3,3-tetramethyl-aminium hexafluorophosphate (HBTU) (100 mmol) and hydroxybenzotriazole (HOBt) (100 mmol) and the reaction mixture was stirred at 20-30° C. In another flask, a homophenylalanine methyl ester hydrochloride (100 mmol) and DMF (150 mL) were charged and the solution cooled at 0-10° C. DIPEA (100 mmol) was slowly added into the solution at 0-10° C. and stirred for 5 min. The solution was carefully transferred to the earlier reaction mixture at 20-30° C. The reaction was maintained at 20-30° C. for 2 hours. MDC (500 mL) was charged, and the mixture was washed with process water (8×100 mL). The organic layer was washed with brine solution (2×100 mL) and the organic layer separated. The organic layer was dried over sodium sulphate (5 g) and distilled under vacuum at below 40° C. Diethyl ether (200 mL) was charged and the mixture cooled at 0-5° C. The separated solid was filtered and dried.

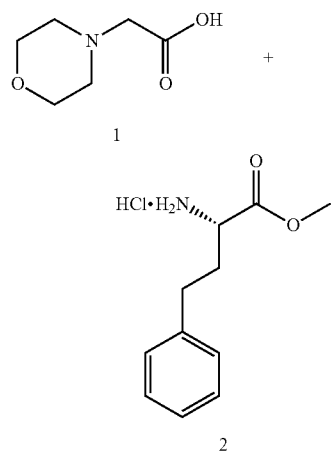

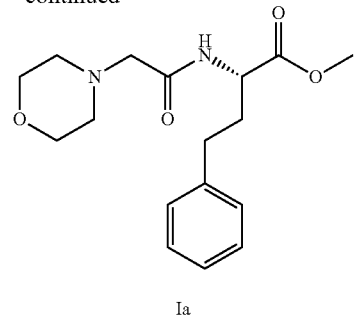

Ia

Example 3(b)

To a 500 mL three-neck round bottom flask equipped with a magnetic stirrer, and thermometer pocket arranged in a tub was charged a chloroacetamido derivative of H-hPhe-OMe (10.0 g), THF (100 mL) and the reaction mixture was stirred at 20-30° C. KI (0.25 equiv.) and morpholine (1.2 equiv.) were added dropwise into the reaction mass at 5-15° C. After 15 minutes the temperature was increased to 20-30° C. The reaction was maintained for 12 to 16 h and upon confirmation of completion of the reaction; the solvent was distilled completely under vacuum at below 40° C. The residue was dissolved in MDC (300 mL) and washed with process water and brine solution. The organic layer was dried over anhydrous sodium sulfate (5 g) and distilled under vacuum at below 40° C. The compound Ia was precipitated with diethyl ether (150 mL) and filtered.

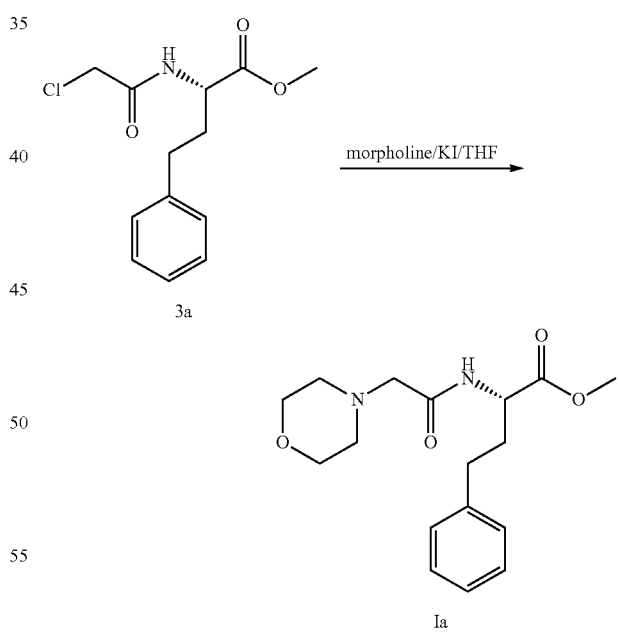

Example 4

Hydrolysis of Morpholine Derivative-Dipeptide Ester

To a 500 mL three-neck round bottom flask equipped with a mechanical stirrer and thermometer pocket arranged in a tub was charged a morpholine derivative dipeptide ester of Formula Ia (100 mmol). Methanol (240 mL) was added and the reaction mixture was stirred at 0-10° C. LiOH (3 equiv.) in process water (80 mL) was added into the reaction mass at 0-10° C. The reaction mixture was maintained for 3-4 h at 0-10° C. The reaction mixture was evaporated to dryness under vacuum and the residue was dissolved with water (100 mL) and washed with ether (100 mL). The aqueous layer was acidified using 3N HCl solution (40 mL). The aqueous layer was extracted with ethylacetate, dried with anhydrous sodium sulphate and evaporated.

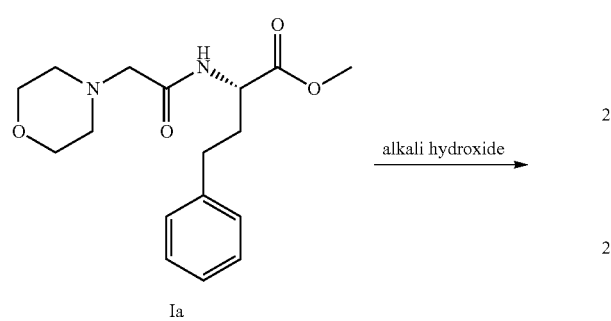

Ia alkali hydroxide

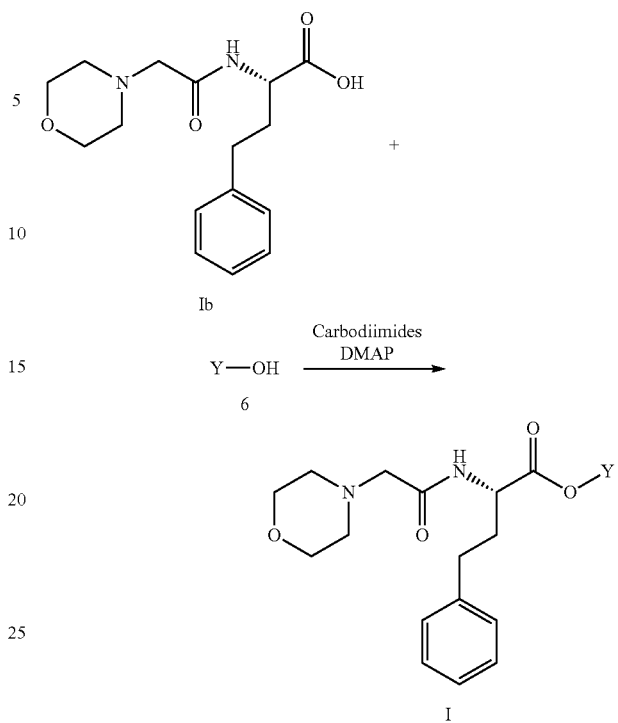

Ib

+

Y—OH

6

Carbodiimides
DMAP

I

Y = pentaflurophenyl, trichlorophenyl, benzatriazole, azabenzotiazole, nitrophenyl, pentachlorophenyl, fluorenylmethyl, etc.,

Example 5

Preparation of Dipeptide Active Ester

To a solution of morpholine-h-phenylalanine-dipeptide (Formula Ib) (100.0 mmol) in 300 ml dry THF, N-(3-dimethylaminopropyl)-N'-ethylcarbodiimide hydrochloride (EDC.HCl) (150 mmol), an N-hydroxy compound/substituted phenol of Formula 6 (100 mmol) wherein Y is 1-hydroxybenzotriazole (OBt) and 4-dimethylaminopyridine (DMAP) (0.1 equiv.) were added, and the reaction mixture was stirred for 2 h at 0° C. After completion of the reaction, confirmed by TLC, the reaction mixture was evaporated to dryness and the residue was dissolved in MDC and washed with process water and brine. The organic layer was dried over anhydrous Na₂SO₄ and the solvent was evaporated under reduced pressure to give a dipeptide ester of the Formula I.

Example 6

Preparation of Boc-hPhe-Leu-OH

To a solution of Boc-hPhe-OH (100.0 mmol, 23.12 g) in 250 ml dry THF, isobutyl chloroformate (100.0 mmol) and NMM (110.0 mmol) were added and the mixture was stirred at 0° C. for 30 min. In another flask, H-Leu-OH (100.0 mmol), TMS-Cl (200 mmol), and DIPEA (200 mmol) were refluxed in 300 mL of dry dichloromethane for 1 h. The mixture was cooled to 0° C. and added in one portion to a preformed mixed anhydride of Formula 5 and the combined reaction mixture was stirred for 30-45 min. The reaction was concentrated under reduced pressure and the residue was dissolved in 10% Na₂CO₃ and washed with ether. The aqueous phase was acidified with citric acid and extracted with 500 mL EtOAc/MDC. The organic layer was washed with water (2×200 mL) and brine (1×200 mL) and dried over anhydrous Na₂SO₄. The solvent was evaporated under reduced pressure to give a dipeptide acid of Formula V.

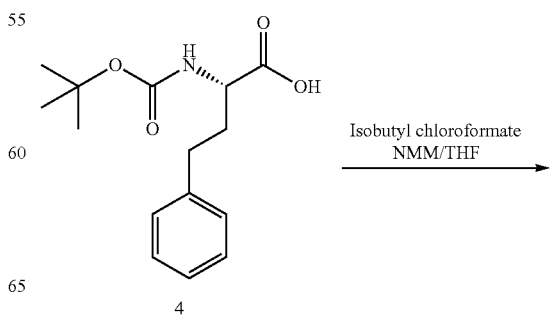

4

Isobutyl chloroformate
NMM/THF

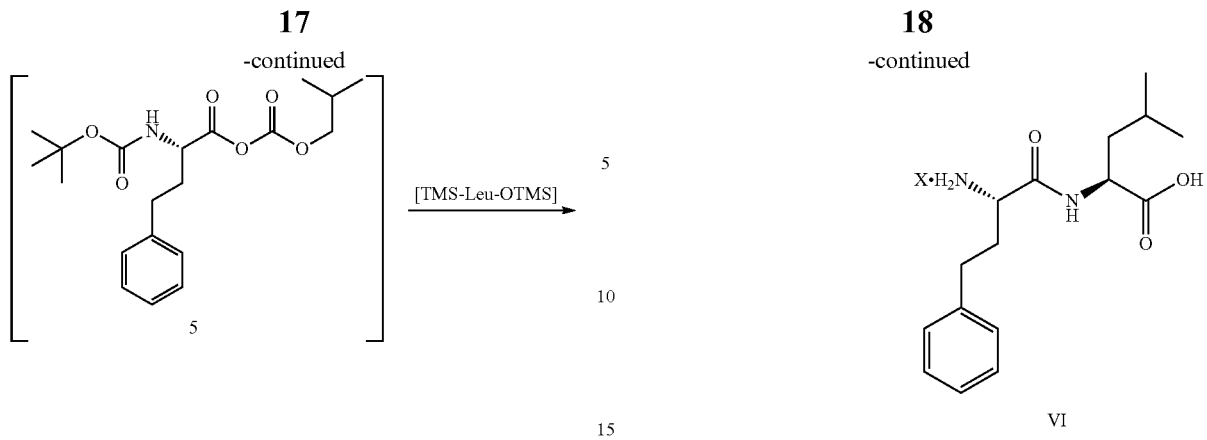

Example 7

Synthesis of H-hPhe-Leu-OH. Salt

To the protected dipeptide of Formula V, was added 80% Trifluoroacetic acid (TFA) in dichloromethane and the reaction mixture was stirred at room temperature for 2 h. Upon confirmation of completion of the reaction monitored by TLC, the mixture was concentrated and the product was precipitated by adding cold ether. The solid was filtered, washed with ether and dried using vacuum. In the scheme below X is TFA.

Example 8

Synthesis of Morpholine Intermediate

To a solution of morpholine-4-yl-acetic acid (100.0 mmol) in 250 ml dry THF, isobutyl chloroformate (100.0 mmol) and NMM (110.0 mmol) were added and the mixture was stirred at 0° C. for 30 min. TFA.H-hPhe-Leu-OH (100.0 mmol), TMS-Cl (200 mmol), and DIPEA (300 mmol) were refluxed in 300 mL of dry dichloromethane for 1 h. The mixture was cooled to 0° C. and added in one portion to the preformed mixed anhydride of Formula 1a and the combined reaction mixture was stirred for 30-45 min. The reaction was concentrated under reduced pressure and the residue was dissolved in 10% $Na_2CO_3$ and washed with ether. The aqueous phase was acidified with citric acid and extracted with 500 mL EtOAc/MDC. The organic layer was washed with water (2×200 mL) and brine (1×200 mL) and dried over anhydrous $Na_2SO_4$. The $Na_2SO_4$ was removed by filtration and the solvent evaporated under reduced pressure to give the tripeptide acid of Formula IIIa.

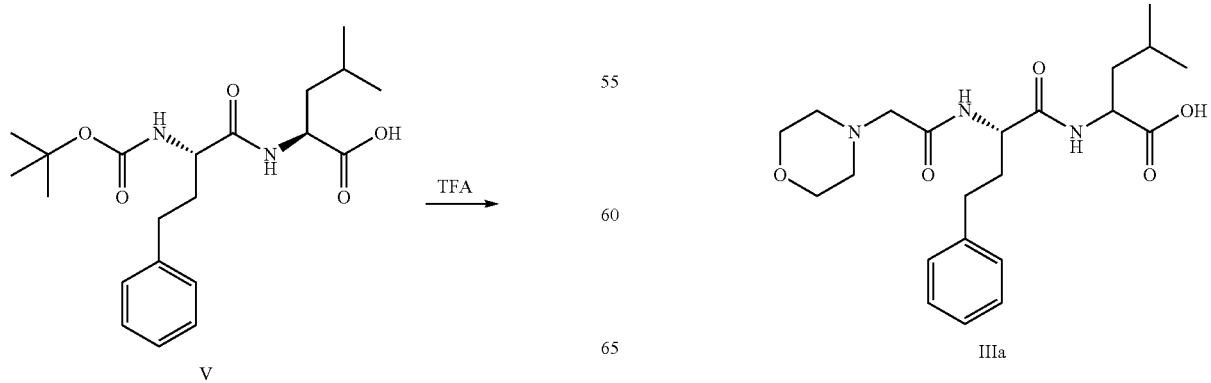

Example 9

Preparation of Tripeptide Active Ester

To a solution of morpholine-hPhe-Leu-OH tripeptide (100.0 mmol) in 300 ml dry THF, EDC.HCl (150 mmol), an N-hydroxy compound/substituted phenol of Formula 6 (100 mmol), and DMAP (0.1 equiv.) were added and the reaction mixture was stirred for 2 h at 0° C. After completion of the reaction, confirmed by TLC, the reaction mixture was evaporated to dryness and the residue was dissolved in MDC and washed with process water and brine. The organic layer was dried over anhydrous $Na_2SO_4$ and the solvent was evaporated under reduced pressure to give the tripeptide ester of the Formula III.

which X is Boc)(100 mmol) and MDC were charged and cooled to 0° C. to 5° C. and trifluoroacetic acid (150 mL) slowly added and stirred for 120 min and distilled under vacuum completely. DMF (150 mL) was charged and the solution cooled at 0-10° C. DIPEA (100 mmol) was slowly added into the solution at 0-10° C. and stirred for 5 min. The solution was carefully transferred to the earlier reaction mixture at 20-30° C. The reaction was maintained for 2 h at 20-30° C. MDC (500 mL) was charged into the reaction mixture, and the mixture was washed with process water (8×100 mL). The organic layer was washed with brine solution (2×100 mL) and the organic layer separated. The organic layer was dried over sodium sulphate (5 g) and distilled under vacuum at below 40° C. Diethyl ether (200 mL) was charged in the vessel and the mixture cooled at 0° C. to 5° C. The separated solid was filtered and dried.

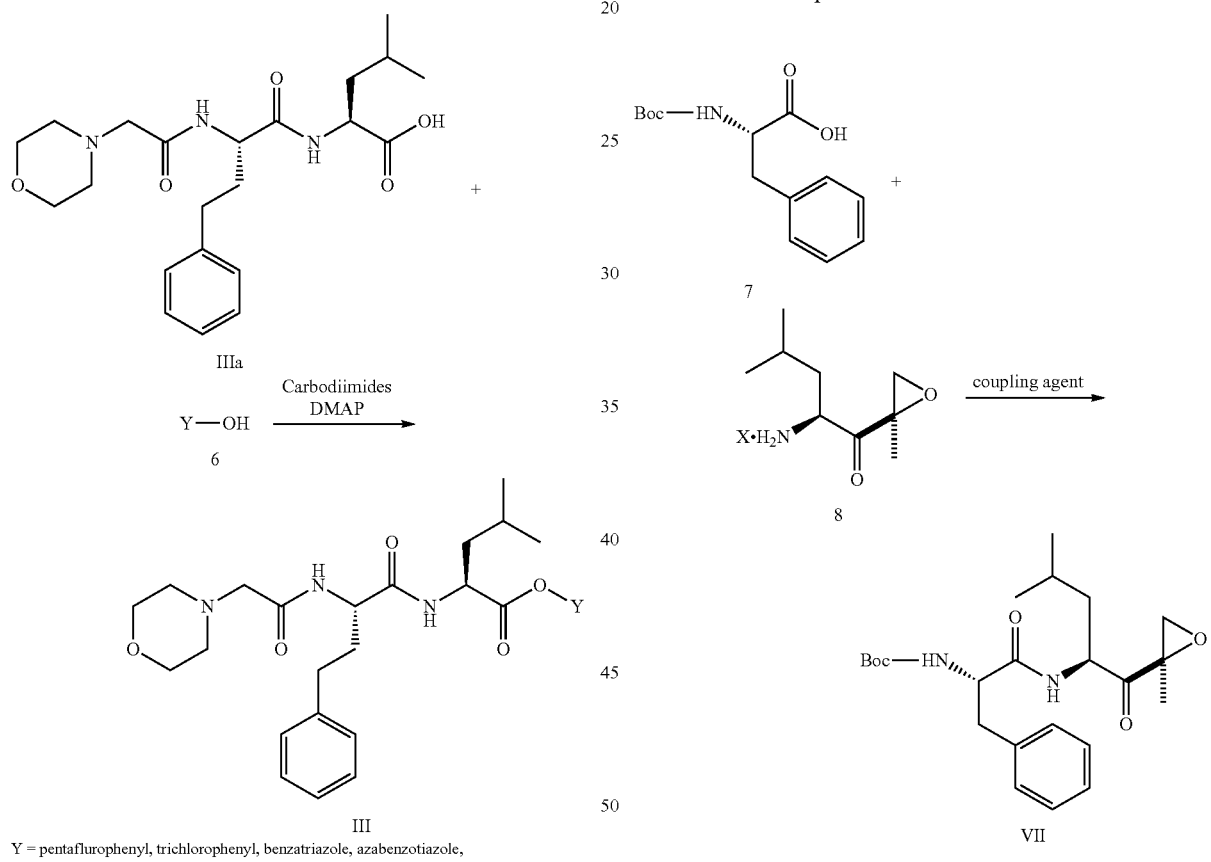

Y = pentaflurophenyl, trichlorophenyl, benzatriazole, azabenzotiazole, nitrophenyl, pentachlorophenyl & fluorenylmethyl,

Example 10

Preparation of Dipeptide with Epoxyketone

A 500 mL single neck flask equipped with a magnetic stirrer was arranged in a tub. Boc-Phe-OH (100 mmol) and DMF (200 mL) were charged into the flask and stirred at 20-30° C. DIPEA (100 mmol) was slowly added into the reaction mixture at 20-30° C., followed by HBTU (100 mmol) and HOBt (100 mmol) which were added and stirred at 20-30° C. In another flask H-Leu-epoxy ketone salt (in

Example 11

Preparation of H-Phe-Leu-Epoxy Ketone Salt

To the protected dipeptide epoxyketone derivative of Formula VII was added 80% TFA in dichloromethane and the reaction mixture was stirred at −10-0° C. for 2 h. Upon confirmation of completion of the deprotection, monitored by TLC, the mixture was concentrated and the product of Formula VIII in which X is TFA was precipitated by adding cold ether. The solid was filtered and washed with ether and dried in vacuum.

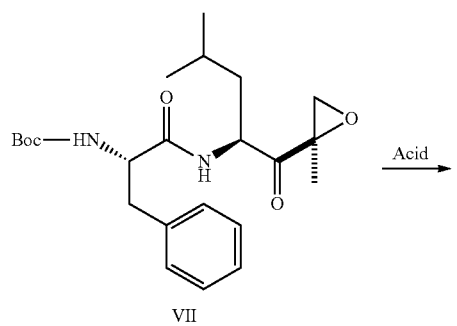

VII

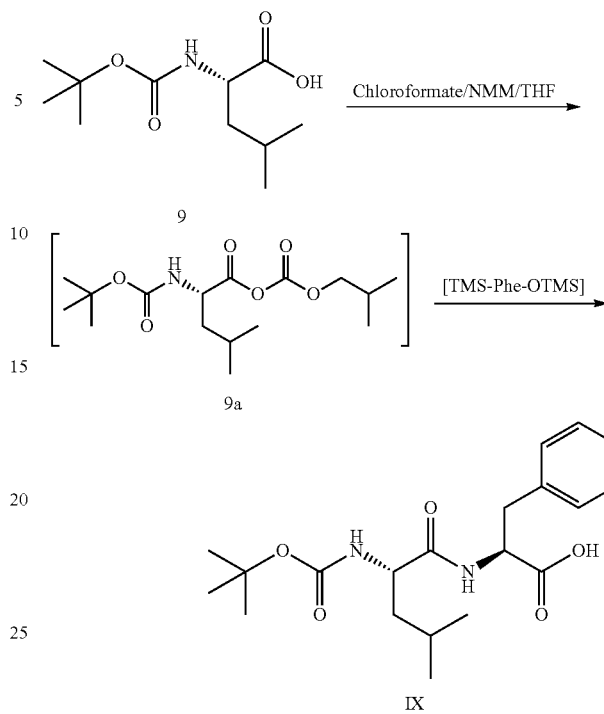

VIII

Example 12

Synthesis of Carfilzomib

To a solution of tripeptide active ester of Formula III (100.0 mmol) in 250 mL organic solvent, a dipeptide epoxyketone derivative of Formula VIII (100 mmol) and equimolar organic base were added. The reaction was stirred at 0-25° C. for 2 h, concentrated under reduced pressure and the residue was dissolved in MDC washed with process water and brine. The organic layer was dried over anhydrous $Na_2SO_4$ and the solvent was evaporated under reduced pressure to obtain the title compound.

Example 13

Preparation of Boc-Leu-Phe-OH

To a solution of Boc-Leu-OH (100.0 mmol) in 250 ml dry THF, isobutyl chloroformate (100.0 mmol) and NMM (110.0 mmol) were added and the mixture was stirred at 0° C. for 30 min. In another flask, H-Phe-OH (100.0 mmol), TMS-Cl (200 mmol), and DDPEA (200 mmol) were refluxed in 300 mL of dry dichloromethane for 1 h. The mixture was cooled to 0° C. and added in one portion to a preformed mixed anhydride of Formula 9a and the combined reaction mixture was stirred for 30-45 min. The reaction was concentrated under reduced pressure and the residue was dissolved in 10% $Na_2CO_3$ and washed with ether. The aqueous phase was acidified with citric acid and extracted with 500 mL EtOAc/MDC. The organic layer was washed with water (2×200 mL) and brine (1×200 mL) and dried over anhydrous $Na_2SO_4$. The solvent was evaporated under reduced pressure to give the dipeptide acid of Formula IX.

Example 14

Preparation of H-Leu-Phe-OH.Salt

To the protected Boc-Leu-Phe-OH dipeptide of Formula IX was added 80% TFA in dichloromethane and the reaction mixture was stirred at room temperature for 2 h. Upon confirming completion of the deprotection (monitored by TLC), the mixture was concentrated and the product was precipitated by adding cold diethyl ether. The solid of Formula X (in which X is TFA) was filtered, washed with ether and dried using vacuum.

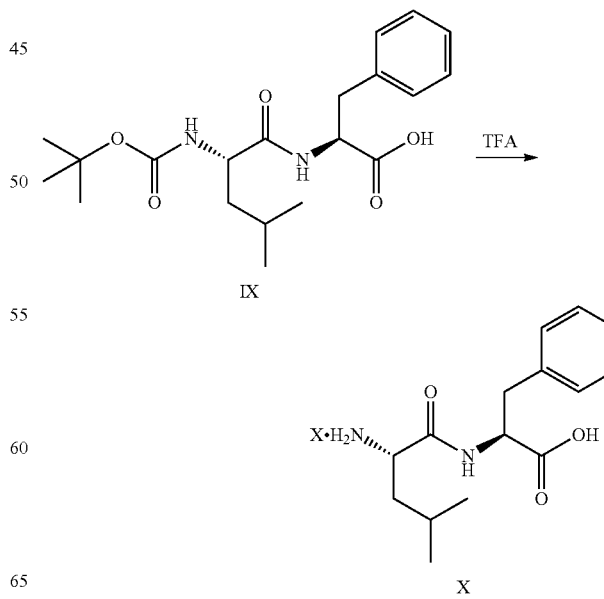

Example 15

Synthesis of Morpholine Derivative of Tetrapeptide

To a solution of morpholine derived dipeptide of Formula Ib (100.0 mmol) in 250 ml dry THF, isobutyl chloroformate (100.0 mmol) and NMM (110.0 mmol) were added and the mixture was stirred at 0° C. for 30 min. In the other flask, TFA.H-Leu-Phe-OH (100.0 mmol), TMS-Cl (200 mmol), and DIPEA (300 mmol) were refluxed in 300 mL of dry dichloromethane for 1 h. The mixture was cooled to 0° C. and added in one portion to the preformed mixed anhydride of Formula Ic and the combined reaction mixture was stirred for 1 h. The reaction was concentrated under reduced pressure and the residue was dissolved in 10% Na$_2$CO$_3$ and washed with ether. The aqueous phase was acidified with 1N HCl and extracted with 500 mL MDC. The organic layer was washed with water (2×200 mL) and brine (1×200 mL) and dried over anhydrous Na$_2$SO$_4$. The Na$_2$SO$_4$ was removed by filtration and the solvent evaporated under reduced pressure to give the tetrapeptide acid of Formula XI.

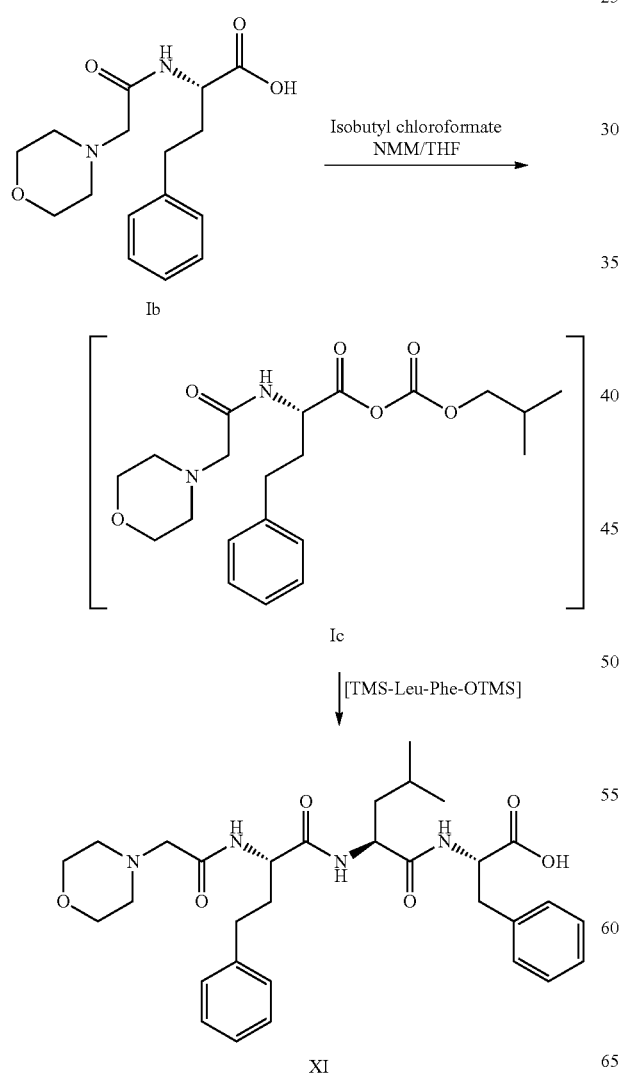

Example 16

Synthesis of Boc-Leu-Phe-OMe

A 500 mL single neck flask equipped with a magnetic stirrer was arranged in a tub. Boc-Leu-OH of the formula 9 (100 mmol) and DMF (200 mL) were charged into the flask and stirred at 20-30° C. DIPEA (100 mmol) was slowly added into the reaction mixture at 20-30° C., followed by HBTU (100 mmol) and HOBt (100 mmol) which were added and stirred at 20-30° C. In another flask H-Phe-OMe salt of the formula 10 (100 mmol) and DMF (150 mL) were charged and the solution cooled at 0-10° C. DIPEA (100 mmol) was slowly added into the solution at 0-10° C. and stirred for 5 min. The solution was carefully transferred to the earlier reaction mixture at 20-30° C. The reaction was maintained for 2 h at 20-30° C. MDC (500 mL) was charged into the reaction mixture, and the mixture was washed with process water (8×100 mL). The organic layer was washed with brine solution (2×100 mL) and the organic layer separated. The organic layer was dried over sodium sulphate (5 g) and distilled under vacuum at below 40° C. Diethyl ether (200 mL) was charged in the vessel and the mixture cooled at 0° C. to 5° C. The separated solid product of Formula XII in which R is CH3 was filtered and dried.

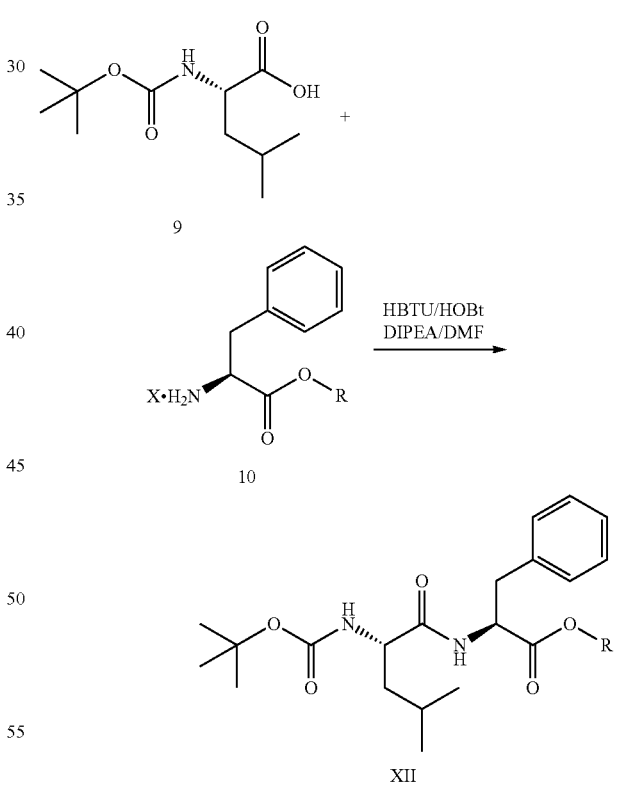

Example 17

Synthesis of H-Leu-Phe-OR. Salt

To the protected Boc-Leu-Phe-OR dipeptide of Formula XII in which R is CH3 was added 80% TFA in dichloromethane and the reaction mixture was stirred at room temperature for 2 h. Upon confirming completion of the deprotection (monitored by TLC), the mixture was concentrated and the product was precipitated by adding cold diethyl ether. The solid of Formula XIII in which X is TFA and R is CH3 was filtered, washed with ether and dried using vacuum.

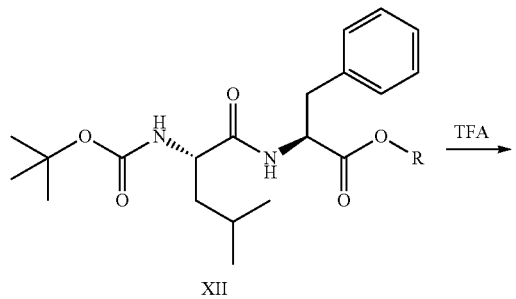

XII

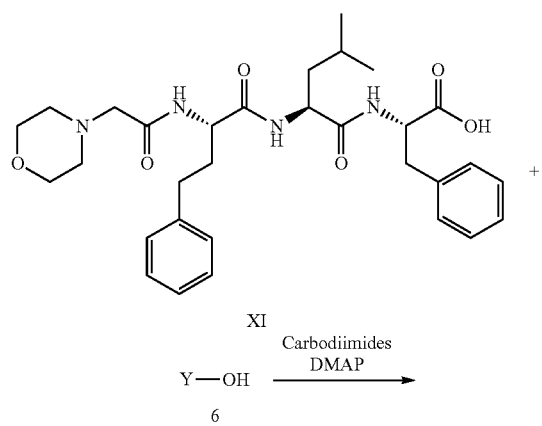

XIII

Example 18

Synthesis of Tetrapeptide Active Ester

To a solution of a morpholine-hPhe-Leu-Phe-OH tetrapeptide of Formula XI (100.0 mmol) in 300 mL dry THF, EDC.HCl (150 mmol), an N-hydroxy compound/substituted phenol of the Formula 6 (100 mmol) and DMAP (0.1 equiv.) were added and the reaction mixture was stirred for 2 h at 0-25° C. After completion of the reaction, confirmed by TLC, evaporated the reaction mixture to dryness and the residue was dissolved in MDC and washed with process water and brine. The organic layer was dried over anhydrous $Na_2SO_4$ and this organic layer used in Example 19.

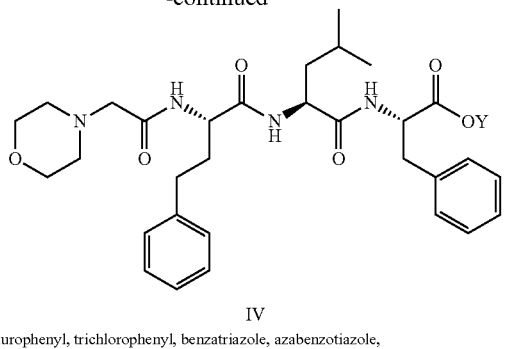

IV

Y = pentaflurophenyl, trichlorophenyl, benzatriazole, azabenzotiazole, nitrophenyl, pentachlorophenyl, fluorenylmethyl,

Example 19

Synthesis of Carfilzomib

The solution of tetrapeptide active ester of the Formula IV (100.0 mmol) from the above example was cooled at 0° C. to 5° C. H-Leu-epoxy ketone derivative of Formula 8 (100 mmol) and MDC were charged in a vessel and cooled to 0° C. to 5° C., and to this mixture trifluoroacetic acid (150 mL) was added slowly and stirred for 120 min and distilled under vacuum completely, and an equimolar quantity of diisopropylethylamine was added. This solution was slowly added to the above solution containing the tetrapeptide active ester of Formula IV. The reaction was stirred at 0-25° C. for 2 h, concentrated under reduced pressure and the residue was dissolved in MDC and washed with process water and brine. The organic layer was dried over anhydrous $Na_2SO_4$ and the solvent was evaporated under reduced pressure to compound carfilzomib.

Example 20

Purification of Carfilzomib

Carfilzomib crude was dissolved in dimethylformamide, a polar aprotic solvent. Examples of suitable polar aprotic solvents include but are not limited to dimethylformamide, dimethylsulfoxide, or acetonitrile. To the solution was added 10% to 20% of citric acid solution. The resulting solution was stirred for 5 to 6 hours then filtered off to obtain the pure carfilzomib. This purification method provides highly pure carfilzomib in which the diasteromeric impurity is controlled at 5 to 10 percent. This method improves yield and reduces the time cycle in scale up purifications.

The purified carfilzomib is further purified by preparative HPLC to obtain the drug substance of carfilzomib with amorphous form. The eluted fractions from preparative HPLC were collected and made pH basic, preferably 8-10, most preferably 8-9. The resulting reaction mass was distilled off in such a way to remain 40% of reaction mass, under vacuum at below 30° C. and stirred for 60 to 90 minutes. Filtered off the reaction mass and again the wet solids were dissolved in MDC and treated with brine solution and sodium sulphate. The resulting reaction mass was subjected to distillation and strip out with diethyl ether. Finally the compound was dried under vacuum to obtain the drug substance of carfilzomib with amorphous form. The XRD profile of the compound is shown in FIG. 1.

Although the compositions and methods of the present disclosure have been described with reference to exemplary embodiments thereof, the present disclosure is not limited thereby. Indeed, the exemplary embodiments are implementations of the disclosed compositions and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

What is claimed is:

1. A compound of the formula IA

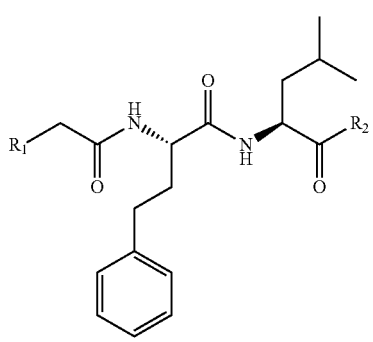

and active esters or salts thereof
wherein R1 is Cl or

and R2 is

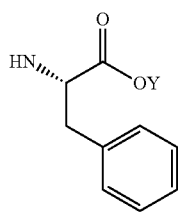

or OY and Y is 1-hydroxybenzotriazole, azabenzotriazole, succinimidyl, pentafluorophenyl, trichlorophenyl, nitrophenyl, pentachlorophenyl, 3,4-dehydro-4-oxo-1,2,3-benzotriazinyl (Dhbt) or fluorenylmethyl.

2. A compound according to claim 1 of the formula II

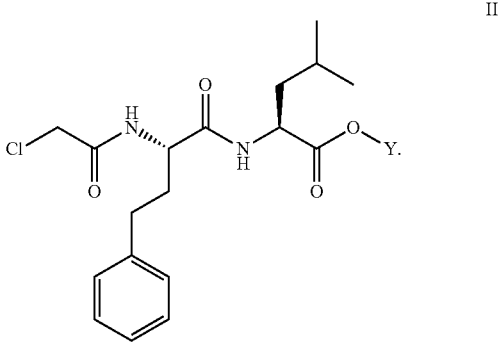

3. A compound according to claim 1 of the formula III

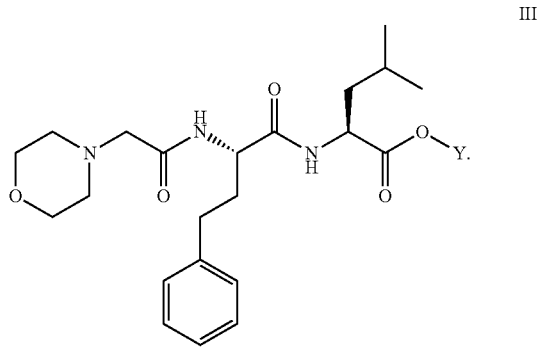

4. A compound according to claim 1 of the formula IV

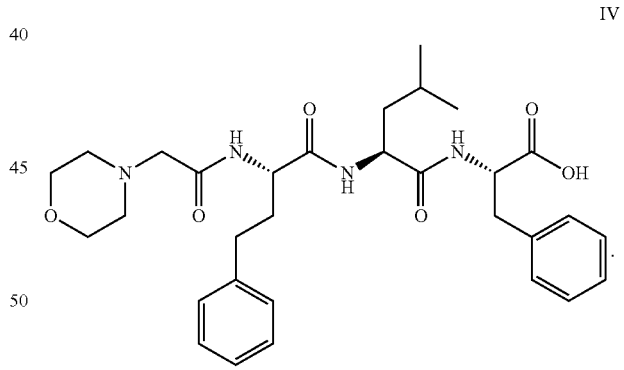

5. A compound according to claim 1 obtained from a corresponding hydroxy compound and/or substituted phenol.

6. A method of making an active ester compound according to claim 1 comprising obtaining a free acid of a compound of formula IA and activating a resulting intermediate using a hydroxy and/or phenolic compound.

7. The method according to claim 6 wherein the step of obtaining a free acid is selected from one or more of bis-silylation, using at least one silylating agent and an organic base, and/or hydrolysis of esters by using at least one alkali metal hydroxide selected from NaOH, KOH, LiOH and their corresponding carbonates.

8. The method according to claim 6 comprising isolating a compound of formula IA using an organic solvent.

9. A method of making carfilzomib comprising employing a compound according to claim 1 using a 3+2 fragment condensation.

10. A method of making carfilzomib comprising employing a compound according to claim 2 using a 3+2 fragment condensation.

11. A method of making carfilzomib comprising employing a compound according to claim 3 using a 3+2 fragment condensation.

12. A method of making carfilzomib comprising employing a compound according to claim 4 using a 3+2 fragment condensation.

13. A method of making amorphous form carfilzomib comprising reacting a compound having the formula I

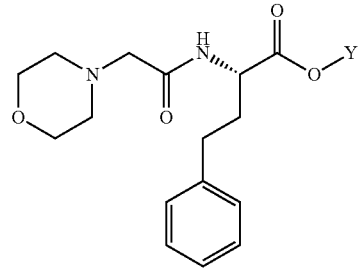

I or an ester or salt thereof, wherein Y is 1-hydroxybenzotriazole, azabenzotriazole, succinimidyl, pentafluorophenyl, trichlorophenyl, nitrophenyl, pentachlorophenyl, 3,4-dehydro-4-oxo-1,2,3-benzotriazinyl (Dhbt) or fluorenylmethyl, with a compound of formula XIII

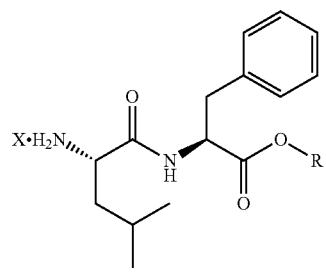

XIII wherein R is H, methyl, ethyl, benzyl, or isopropyl and X is HCl, TFA, HCOOH, TsOH or MsOH to obtain a compound of formula IV

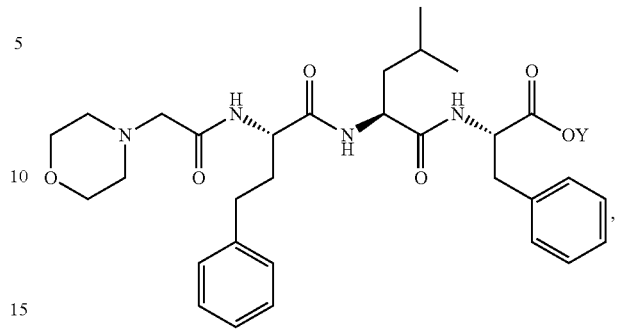

IV and reacting a compound of formula IV with a compound of formula 8

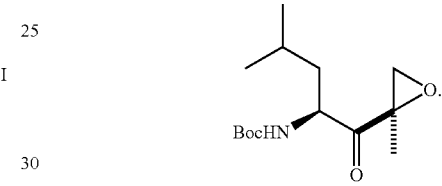

8

14. A method of making amorphous form carfilzomib comprising the synthetic route:

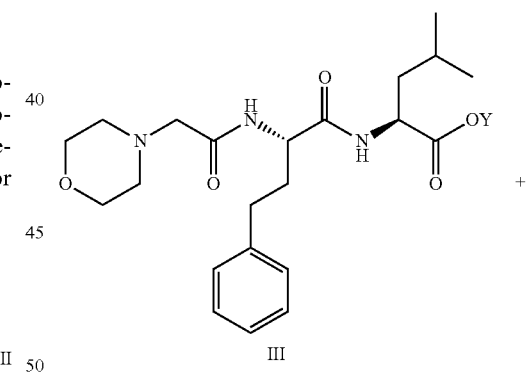

III

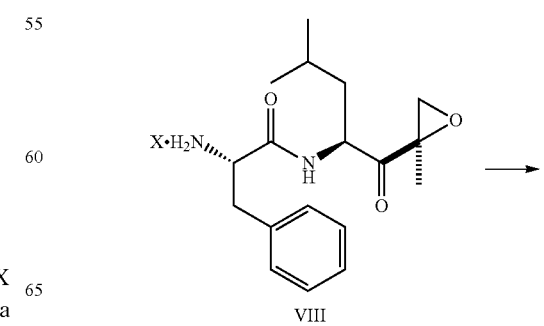

VIII

-continued

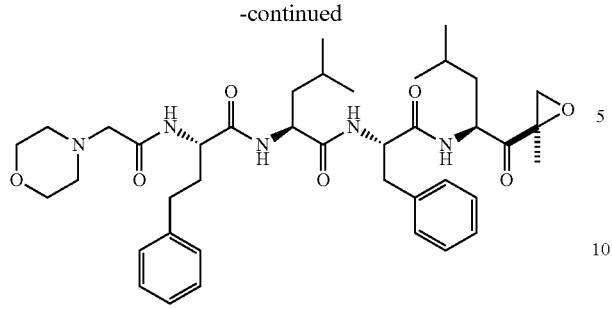

Carfilzomib wherein Y is 1-hydroxybenzotriazole, azabenzotriazole, succinimidyl, pentafluorophenyl, trichlorophenyl, nitrophenyl, pentachlorophenyl, 3,4-dehydro-4-oxo-1,2,3-benzotriazinyl (Dhbt), or fluorenylmethyl and X is HCl, TFA, HCOOH, TsOH, MsOH or isopropyl (IPr).

15. The method according to claim 14 comprising isolating amorphous carfilzomib using organic solvent extraction.

* * * * *